United States Patent [19]
Ambrosius et al.

[11] Patent Number: 5,856,156
[45] Date of Patent: *Jan. 5, 1999

[54] MICROBIAL CHOLESTEROL DEHYDROGENASE, PROCESS FOR ITS PRODUCTION AND USE

[75] Inventors: Dorothee Ambrosius, München; Klaus Kaluza, Bad Heilbrunn; Stephan Gross, München, all of Germany

[73] Assignee: Boehringer Mannheim GmbH, Mannheim, Germany

[*] Notice: This patent issued on a continued prosecution application filed under 37 CFR 1.53(d), and is subject to the twenty year patent term provisions of 35 U.S.C. 154(a)(2).

[21] Appl. No.: 546,781

[22] Filed: Oct. 23, 1995

Related U.S. Application Data

[63] Continuation of Ser. No. 546,781, Oct. 23, 1995, abandoned.

[30] Foreign Application Priority Data

Oct. 26, 1994 [DE] Germany .............................. 44 38 206

[51] Int. Cl.⁶ ...................................................... C12N 9/02

[52] U.S. Cl. .............................. 435/189; 435/190; 435/25; 435/26; 424/94.4

[58] Field of Search ................................. 435/189, 25, 26, 435/190; 424/94.4

[56] References Cited

U.S. PATENT DOCUMENTS 5,128,247  7/1992  Palmer et al. .............................. 435/25

FOREIGN PATENT DOCUMENTS

| 2649749 | 5/1978 | Germany . |
| 1412244 | 10/1973 | United Kingdom . |
| 82/00833 | 3/1982 | WIPO . |

OTHER PUBLICATIONS

Hesselink et al., J. Steroid Biochem., vol. 35, No. 1. pp. 107–113, 1990.

*Primary Examiner*—Irene Marx
*Attorney, Agent, or Firm*—Fulbright & Jaworski LLP

[57] ABSTRACT

Oxygen-independent cholesterol-converting enzyme obtainable from Actinomycetes or Basidiomycetes which utilizes artificial electron acceptors as well as a method and reagent for the determination of (total) cholesterol using the enzyme.

7 Claims, 1 Drawing Sheet

MICROBIAL CHOLESTEROL DEHYDROGENASE, PROCESS FOR ITS PRODUCTION AND USE

This application is a continuation, of application Ser. No. 08/546,781 filed Oct. 23, 1995, now abandoned.

BACKGROUND OF THE INVENTION

Field of the Invention

The invention concerns an oxygen-independent cholesterol-converting enzyme, a process for its isolation from particular microorganisms as well as the use of the enzyme to determine cholesterol.

The quantitative determination of cholesterol in blood with the aid of enzymatic tests has for a long time been a proven method in clinical chemistry (Flegg 1973, Richmond 1973). A cholesterol oxidase is usually used as the enzyme which catalyses the oxidation of cholesterol (5-cholesten-3-β-ol) to 4-cholesten-3-one and $H_2O_2$.

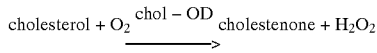

In this case oxygen serves as an electron acceptor. The provision of this enzyme on an industrial scale from microorganisms of the Schizophyllum, Streptoverticillium, Brevibacterium, Nocardia, Rhodococcus or *streptomyces* classes (Noma & Nakayama 1976, EP 0560 983; Liu et al. 1980, Ishizaki 1989, Halpern 1981, Aihara et al. 1986, Fujishiro et al. 1990, EP 0452 112) is established.

However, the oxygen dependency of cholesterol oxidase is a major disadvantage and the main reason for test inaccuracies. It often causes problems in calibrating the test since the dependency on oxygen partial pressure results in an altitude dependency as well as in a temperature dependency of the test.

In addition the quantitative determination of cholesterol from blood with the aid of cholesterol oxidases by means of a coupled colour reaction is susceptible to interference due to the $H_2O_2$ that is formed: $H_2O_2$ is removed from the reaction equilibrium due to its high reactivity with for example bilirubin or drugs.

An oxygen-independent cholesterol-converting enzyme, i.e. a NAD- or NADP-dependent cholesterol dehydrogenase which is obtainable from an anaerobic microorganism (Eubacterium sp.) or from liver tissue of warm-blooded animals, is described in DE 2649749. The major disadvantage of the enzyme described in this application is that the enzyme also has to be isolated under an inert gas atmosphere. A scale-up of the process and the provision of the said enzyme on a larger scale is not feasible. Moreover, the enzyme requires NAD(P) as a cofactor so that an additional reaction step (enzymatic or chemical) is necessary for colour formation. This usually results in an increase in costs and a higher susceptibility to interference. Appropriate NAD(P)-independent dehydrogenases have been previously known only for other substrates such as for example glucose or glycerol (Duine 1991, Ameyama et al. 1985, Ameyama 1982, EP 0354 441, Ameyama et al. 1981, EP 0 120 440).

OBJECTS AND SUMMARY OF THE INVENTION

The object of the invention is therefore to provide a cholesterol-converting enzyme which overcomes the aforementioned disadvantages.

The object is achieved by a cholesterol-converting enzyme which uses artificial electron acceptors (mediators) and is obtainable from particular microorganisms. In particular unsubstituted or substituted benzoquinones, indophenol and nitrosoaniline derivatives come into consideration as artificial electron acceptors (mediators). Among the substituted benzoquinone and nitrosoaniline compounds those are preferred which carry non-electron-withdrawing residues on the aromatic backbone such as for example lower alkyl groups. Alkyl groups with up to 10 C atoms have proven to be particularly suitable in this case.

In particular methyl-1,4-benzoquinone (MBQ), p-benzoquinone (PBQ) and N,N-dimethyl-4-nitrosoanaline (NA), but also 2,6-dichlorophenol-indophenol (DCIP) and N,N-bis-2(hydroxyethyl)-p-nitrosoaniline have proven to be suitable as artificial electron acceptors.

The main advantage of the enzyme according to the invention is that instead of transferring electrons onto oxygen or NAD(P) it transfers them directly onto artificial electron acceptors which can be utilized directly for signal yield. In contrast to classical test methods using cholesterol oxidase, the measuring system is independent of the oxygen partial pressure. Thus an oxygen interference is avoided.

The enzyme according to the invention occurs in particular in microorganisms such as Actinomycetes or Basidiomycetes species. In particular it was possible to isolate an appropriate cholesterol dehydrogenase (chol-DH) from particular Rhodococcus and Streptomyces strains Rhodococcus spec., BMTU 3899, Accession Number DSM 9444, which was deposited in the Deutsche Samlung Von Mikroorganismen und Zellkulturen GmbH, Mascheroder Weg 1B, D-3300, Braunschweig, on Sep. 20, 1994; *Rhodococcus erythropolis* Accession Number DSM 743, which was deposited in the Deutsche Sammlung Von Mikroorganismen und Zellkulturen GmbH, Mascheroder Weg 1B, D-3300, Braunschweig, on Aug. 30, 1976; *Streptomyces hygroscopicus* Accession Number DSM 40771, which was deposited in the Deutsche Sammlung Von Mikroorganismen und Zellkulturen GmbH, Mascheroder Weg 1B, D-3300, Braunschweig, on Apr. 15, 1975). In the case of fungal strains particular Basidiomycetes species (*Flammulina velutipes* Accession Number DSM 1658, which was deposited in the Deutsche Sammlung Von Mikroorganismen und Zellkulturen GmbH, Mascheroder Weg 1B, D-3300, Braunschweig, on Sep. 24, 1979; *Coprinus comatus* Accession Number DSM 1746, which was deposited in the Deutsche Sammlung Von Mikroorganismen und Zellkulturen GmbH, Mascheroder Weg 1B, D-3300, Braunschweig, on Feb. 6, 1980; *Trametes versicolor* BMTU 3107, Accession Number DSM 9443, which was deposited in the Deutsche Samlung Von Mikroorganismen und Zellkulturen GmbH, Mascheroder Weg 1B, D-3300, Braunschweig, on Sep. 20, 1994) have proven in the main to be suitable as a source for the cholesterol dehydrogenase according to the invention.

The enzyme according to the invention is in addition characterized by an optimal pH value range of 6 to 10 and an optimal temperature between 25° C. and 40° C. In addition the enzyme exhibits a high temperature stability: without addition of a stabilizer the enzyme still has at least 90% and usually still 98–100% of its initial activity after ca. 30 minutes at 60° C. (FIG. 1). The chol-DH according to the invention exhibits the highest pH stability in the range of pH 7.0 to 8.0 (FIG. 2).

Moreover the enzyme is characterized by an apparent molecular weight of approximately 55,000 Da (SDS-PAGE). The isoelectric point of the chol-DH is at about pH 8.6 (Amphilie PAG plate pH 3.5 9.5; 2,5 hours, 1500 V, 30 mA and 30 W).

The invention in addition concerns a process for producing cholesterol dehydrogenase in which suitable bacterial or fungal strains that contain a cholesterol dehydrogenase are firstly cultured in a suitable growth medium. A suitable growth medium is based on a yeast extract basis and contains cholesterol at concentrations of ca. 0.5–5 g/l in addition to the other usual nutrient salts and trace elements. Particularly when growing bacterial strains a doubling of the expression could be achieved with tryptic soy (Difco, article No. 0370). In addition a further increase of expression by a factor of 4 was achieved by adding detergents (0.1–5%; (w/v)) such as for example Tween 80. In this case taurocholate has also proven to be suitable. The enzyme is subsequently isolated from the culture supernatant by means of fractionated ammonium sulfate precipitation, dialysis and one or several chromatographic purification steps. In particular it has proven to be advantageous for the chromatographic purification of chol-DH when firstly a hydroxyapatite and subsequently a phenylsepharose and Superdex 200 column is used. The isolation of the enzyme from the biomasses is carried out analogously using in addition a suitable lysis buffer and measures for cell disruption. In this process the cells can be disrupted chemically, enzymatically (e.g. lysozyme treatment) or mechanically (pressure, cell grinder, glass beads etc.). After cell disruption and extraction of the enzyme with organic solvent it is advantageous to wash the enzyme fraction.

In this manner chol-DH could be obtained with a purity of at least 99% (for example SDS-PAGE or RP-HPLC; the methods are known to a person skilled in the art), a specific activity of 2 to 3 U/mg and a yield of ca. 10% (relative to the dialysate after ammonium sulfate precipitation i.e. after separation of higher molecular components such as lipids etc.).

The invention in addition concerns the use of the enzyme according to the invention to determine total cholesterol (free or bound) in biological samples such as those that are used in clinical chemistry. In this process the chol-DH activity is either determined via the formation of cholestenone or via the reduction of the added redox mediator. Formation of cholestenone is monitored for example with the aid of a HPLC method or the reduction of the redox mediator is monitored photometrically or electrochemically.

A corresponding reagent for the determination of total cholesterol (free or bound) is usually composed of cholesterol esterase, oxygen-independent cholesterol dehydrogenase, buffer, if necessary a stabilizer or/and a surface-active agent, and a system for determining cholestenone or the reduced mediator. Appropriate systems for determining cholestenone are known to a person skilled in the art. The determination of the reduced mediator can be carried out directly and namely by determination of the decrease in absorbance at a wavelength between 300 and 700 nm depending on the mediator used. When using DCIP, PBQ or MBQ the decrease in absorbance is monitored spectroscopically at a wavelength of approximately 600 nm.

The quantitative composition of such a reagent is appropriately 0.02 to 4 U/ml cholesterol esterase, 0.02 to 4 U/ml oxygen-independent chol-DH and 0.01 to 10 mM of an electron acceptor preferably 0.05 to 1 mM.

If the reagent contains a surface-active agent such as for example Thesit or cholate, then it is expedient that its concentration is between 0.1 and 10% (w/v).

The method and reagent according to the invention enable a very rapid and complete determination of bound and free cholesterol in particular also in biological samples such as serum, blood, plasma and such like. A particular advantage is that no additional measuring reactions have to be coupled to this and the determination can be carried out directly with the widespread simple photometers.

BRIEF DESCRIPTION OF THE INVENTION

FIG. 1: Stability of chol-DH (1.0 U/ml) under temperature stress; 30 min incubation in water baths at the appropriate temperature; the chol-DH activity is stated relative to the initial activity FIG. 2: Stability of chol-DH (1.0 U/ml) when stressed for 3 h at 25° C. under various pH conditions the chol-DH activity is stated relative to the initial activity;

buffers used: pH 3.0–6.0: 0.2M $Na_2HPO_4$/citrate buffer pH 7.0–9.0: 0.2M $K_2HPO_4$/KOH buffer

REFERENCES

1. Flegg, H. M. (1973) An investigation of the determination of serum cholesterol by an enzymatic method. Ann. Clin. Biochem. 10: 79
2. Richmond, W. (1973) Preparation and properties of a cholesterol oxidase from Nocardia sp. and its application to the enzymatic assay of total cholesterol in serum. Clin. Chem. 19: 1350–1356
3. Noma, A. & Nakayama, K. (1976) Comparative studies on cholesterol oxidases from different sources. Clin. Chim. Acta 73: 487–496
4. Liu, W., Cheng, C. & Su, Y. (1980) Isolation and identification of a cholesterol oxidase-producing bacterium Proc. Natl. Sci. Counc. ROC 4: 433–437
5. Ishizaki, T., Hirayama, N., Shinkawa, H., Nimi, O. & Murooka, Y. (1989) Nucleotide sequence of the gene for cholesterol oxidase from a Streptomyces sp. J. Bacteriol. 171: 596–601
6. Halpern, M. G. (1981) Cholesterol oxidase from bacteria. pp. 3–22; In: Industrial Enzymes from Microbial Sources, Noyes Data Corporation
7. Aihara, H., Watanabe, K. & Nakamura, R. (1986) Characterization of production of cholesterol oxidases in three Rhodococcus strains. J. Appl. Bacteriol. 61: 269–274
8. Fujishiro, K., Ohta, T., Hasegawa, M., Yamaguchi, K., Mizukami, T. & Uwajima, T. (1990) Isolation and identification of the gene of cholesterol oxidase from *Brevibacterium sterolicum* ATCC 21387, a widely used enzyme in clinical analyses. Biochem. Biophys. Research Communications 172: 721–727
9. Fujishiro, K. & Uwajima, T. (1991) Cholesterol oxidase. EP 0 452 112 A1
10. Duine, J. A. (1991) Quinoproteins: Enzymes containing the quinonoid cofactor pyrroloquinoline quinone, topaquinone or tryptophan-tryptophan quinone. Eur. J. Biochem. 200: 271–284
11. Ameyama, M., Shinagawa, E., Matsushita, K. & Adachi, O. (1985) Solubilization, purification and properties of membrane-bound glycerol dehydrogenase from *Gluconobacter industrius*. Agric. Biol. Chem. 49: 1001–1010
12. Ameyama, M. (1982) Enzymatic microdetermination of D-glucose, D-fructose, D-gluconate, 2-keto-D-gluconate, aldehyde, and alcohol with membrane-bound dehydrogenases. Methods Enzymol. 28: 20–29
13. Ameyama, M. (1990) NAD(P)-unabhängige Glycerindehydrogenase, Verfahren zu deren Herstellung sowie deren Verwendung zur Bestimmung von Glycerin und Triglyceriden. EP 0 120 440 B1.
14. Ameyama, M., Shinagawa, E., Matsushita, K. & Adachi, O. (1981) D-glucose dehydrogenase of *Gluconobacter*

*suboxydans:* Solubilization, purification and characterization. Agric. Biol. Chem. 45: 851–861

15. Hoenes, J. (1990) Verfahren zu kolorimetrischen Bestimmung eines Analyten mittels enzymatischer Oxidation. EP 0 354 441 A1

DESCRIPTION OF THE PREFERRED EMBODIMENT(S)

Figure 1:
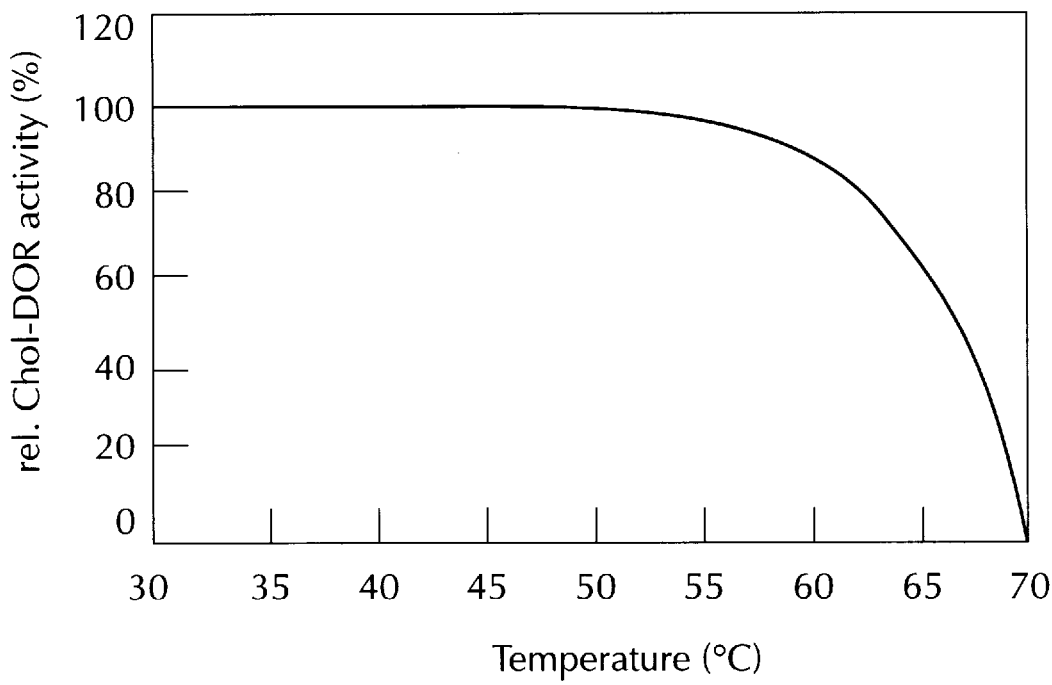
Figure 2:
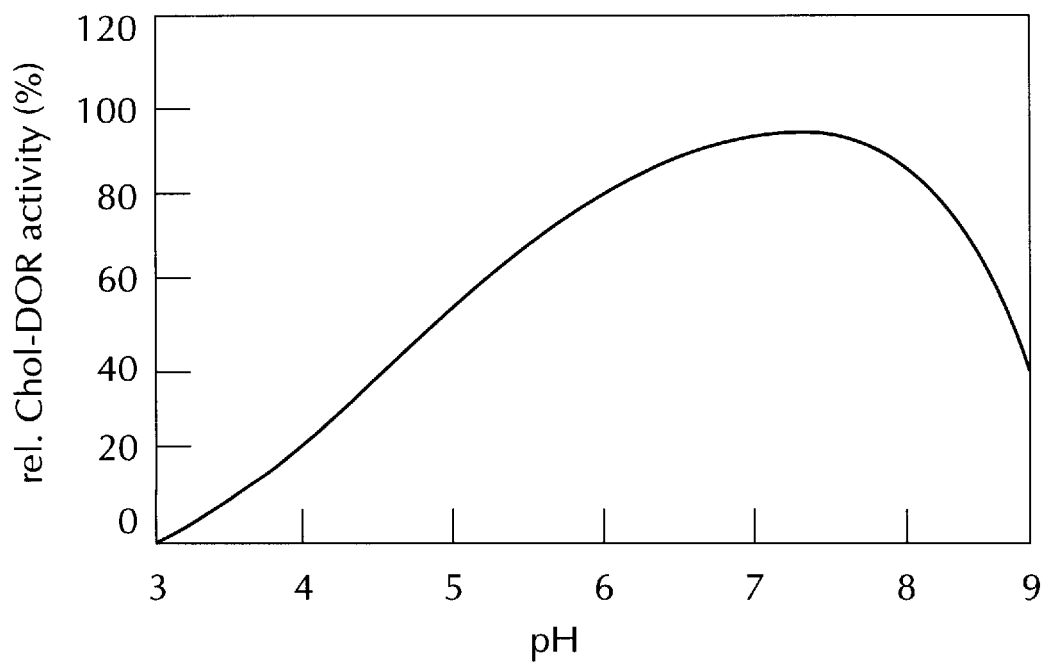

The invention is further elucidated by the following examples.

EXAMPLE 1

Culture of microorganisms that contain a cholesterol dehydrogenase 1.1 Bacteria

Cholesterol dehydrogenase could for example be isolated from the following organisms:

*Rhodococcus erythropolis* Accession Number DSM 743)

*Rhodococcus* spec. BMTU 3899, Accession Number DSM 9444

*Streptomyces hygroscopicus* Accession Number DSM 40771.

*Flammulina velutipes* BMTU 3683, Accession Number DSM 1658.

These bacterial strains were cultured according to known methods: Purity smears of the bacterial strains were set up on standard I nutrient agar plates (Merck article No. 7881). Starting with these purity smears precultures were set up in standard I nutrient broth (Merck article No. 7882).

For this 50 ml nutrient broth in 250 ml Erlenmeyer flasks was inoculated with a single culture of the purity smear and incubated for 24 hours at 28° C. in an incubation room on a horizontal shaker at 150 rpm. These precultures were the starting point for setting up main cultures in the above growth medium. For this 800 ml of the growth medium in 2.0 l Erlenmeyer flasks was inoculated with 15 ml preculture and incubated for 60 h at 28° C. in an incubation room on a horizontal shaker at 150 rpm.

The following growth medium was used; all components of the medium were dissolved in water (dist.).

| Growth medium: | |
|---|---|
| $Na_2HPO_4.2H_2O$ | 5.25 g/l |
| $KH_2PO_4$ | 1.50 g/l |
| NaCl | 0.10 g/l |
| $MgSO_4.7H_2O$ | 0.10 g/l |
| yeast extract | 0.50 g/l |
| $NH_4Cl$ | 1.00 g/l |
| trace elements (solution) | 1.00 ml/l |
| cholesterol solution | 100.00 ml/l |
| Trace elements (solution): | |
| $MnCl_2.4H_2O$ | 0.50 mg/l |
| $ZnSO_4.7H_2O$ | 1.00 mg/l |
| $CuSO_4.5H_2O$ | 0.50 mg/l |
| $COCl_2.6H_2O$ | 0.50 mg/l |
| $NiCl_2.6H_2O$ | 0.50 mg/l |
| $Na_2MoO_4.2H_2O$ | 0.05 mg/l |
| $FeCl_3.6H_2O$ | 1.50 mg/l |
| Cholesterol suspension: | |
| cholesterol | 10.0 g/l |
| Tween 80 | 7.5 g/l |

An enzymatic activity could be measured in the culture supernatants as well as in the biomasses.

1.2 Fungi

Examples of chol-DH from Basidiomyces species

EXAMPLE 1.2.1

20 ml of a nutrient solution containing 0.1% yeast extract (Difco), 0.2% ammonium tartrate, 0.1% $KH_2PO_4$, 0.05% $MgSO_4$, 0.05% KCl and 1% glucose in a 100 ml Erlenmeyer flask was inoculated with *Flammulina velutipes* BMTU 3683, Accession Number DSM 1658. This preculture was incubated for 6 days at 28° C. while shaking.

As the main culture the aforementioned culture was added to 500 ml of a nutrient solution containing 0.5% yeast extract (Difco), 1% malt extract, 0.001% $FeCl_3$, 1% glucose at a pH of 6.0 in a 2 l Erlenmeyer flask and incubated for a further 6 days on a shaker.

After the culture the cells were separated by filtration.

An enzyme activity of 3.5 mU/ml could be detected in the culture supernatant.

Photometric method:

2,6-Dichlorophenol-indophenol (DCIP) was used as a redox mediator to determine the chol-DH activity from Basidiomycetes. The reduction of DCIP was measured by means of the absorbance decrease at 600 nm.

Reagents used:
1. 0.1M MOPS/KOH, pH 7.5
2. 2 mM DCIP in buffer 1
3. 5% Na cholate/5% Na deoxycholate in buffer 1
4. catalase (BM Cat.No. 0156 744)
5. 15 mM cholesterol dissolved in buffer 3

| | Blank | Sample |
|---|---|---|
| buffer 1 | 729 µl | 729 µl |
| DCIP (2) | 66 µl | 66 µl |
| catalase (4) | 5 µl | 5 µl |
| solution (3) | 50 µl | 50 µl |
| enzyme sample (ca. 10 mU/ml) | 50 µl | 50 µl |
| mix and wait until pre-reaction is completed | | |
| cholesterol (5) | | 100 µl |
| solution (3) | 100 µl | |
| mix and measure at $A_{600}$ | | |

The chol-DH activity is determined as follows:

One unit is the enzyme activity which oxidizes 1 µmol cholesterol per minute to cholestenone under the test conditions (37° C., pH 7.0) and concomitantly reduces 1 µmol $DCIP_{ox}$.

$$\text{Volume activity:} \frac{1.0}{16.13 \times 0.05} \text{ dilution factor of}$$

the sample $\Delta A/\min[U/\text{ml sample}]$

EXAMPLE 1.2.2

100 ml of a preculture of *Flammulina velutipes* BMTU 3683 was cultured as described in example 1.2.1 and added to 1.7 l of a nutrient solution containing 0.3% yeast extract (Difco), 1% polypeptone M66 (Merck), 0.3% $KH_2PO_4$, 0.1% $MgSO_4$, 1% glucose in a 5 l wide-necked reagent bottle with conical shoulder. The culture was incubated for 6 days at 28° C. while shaking.

An activity of 2.7 mU/ml was measured in the culture supernatant with a specific activity of 20 mU/mg protein. The supernatant was admixed with 0.1% Tween 80 and concentrated by diafiltration (10 kD membrane, Filtron Ultrasette™). The filtrate that was washed with 20 mM Tris/HCl pH 7.5 in this process, was applied to a 5 cm DEA membrane (Sartorius) and eluted with 0.3M NaCl (eluate 1) or 0.6M NaCl (eluate 2). Eluate 1 contained a total activity of 0.7 U having a specific activity of 0.24 U/mg protein, eluate 2 contained 0.3 U with a specific activity of 1.03 U/mg.

EXAMPLE 1.2.3

20 ml of a nutrient solution containing 0.3% yeast extract, 1% polypeptone (Merck), 0.3% $KH_2PO_4$, 0.1% $MgSO_4$, 1% starch was inoculated with *Trametes versicolor* BMTU 3107, Accession Number DSM 9443.

After 5 days of growth at 28° C., the culture was transferred to 500 ml of the same medium and shaken for a further 5 days in a 2 l Erlenmeyer flask. An activity of 1.5 mU/ml was measured in the culture filtrate.

EXAMPLE 1.2.4

*Coprinus comatus* BMTU 3680, Accession Number DSM 1746 was cultured as described in example 1.2.4. An activity of 0.4 mU/ml was measured in the culture filtrate.

EXAMPLE 2

Isolation of cholesterol dehydrogenase a) Isolation from the supernatant

The culture supernatant of a fermentation of Rhodococcus spec. (Accession Number DSM 9444) was diafiltered (30,000 open-channel membrane) against 50 mM potassium phosphate buffer pH 7.0. The chol-DH was precipitated with the aid of ammonium sulfate from the diafiltrate. In this process foreign proteins were removed in a first step (1.2M ammonium sulfate) and the chol-DH was then precipitated quantitatively with 2.4M ammonium sulfate. The precipitate was dissolved in 10 mM potassium phosphate buffer pH 7.0 and dialysed against this buffer. The chol-DH was purified by chromatography on hydroxylapatite (pH 6.8), phenylsepharose and Superdex-200 (pH 7.0).

In the hydroxylapatite separation the column (V=40 ml) was firstly equilibrated with buffer A (10 mM $KH_2PO_4$/KOH; pH 6.8 plus 0.3 mM $CaCl_2$) at 10° C. and a flow rate of 40 ml/h. A gradient of 200 ml buffer A and of buffer B (350 mM $KH_2PO_4$/KOH; pH 6.8 plus 10 mM $CaCl_2$) was used for the separation. A total of 200 mg protein was applied to the column, the sample having a protein concentration of 5 mg/ml.

Phenylsepharose (10 ml column) which has been equilibrated in starting buffer (50 mM $KH_2PO_4$/KOH; pH 7.0, 1M ammonium sulfate) is suitable as a further purification step. All steps were carried out at 10° C. and a flow rate of one column volume per hour. The column was loaded with 20 mg protein, the protein concentration of the sample being 2 mg/ml. The gradient for the elution was adjusted with the aid of 50 ml starting buffer and 50 ml buffer B (10 mM $KH_2PO_4$/KOH; pH 7.0; 0.1% Thesit).

An additional separation of foreign protein was achieved with the aid of gel permeation chromatography on Superdex-S200. The column was equilibrated at room temperature with 200 mM $KH_2PO_4$/KOH; pH 7.0; 0.1% Thesit at a flow rate of 1 ml/min. After applying a sample volume of 1 ml (≙5 mg protein) separation is achieved with the above-mentioned buffer.

Using the described purification scheme an enzyme sample with a purity of >99% SDS-PAGE (or RP-HPLC) and a specific activity of 2.4 U/mg (based on the activity test in example 3a); protein determination according to Pierce, BCA-assay with a BSA standard) and a yield of 9% (relative to the dialysate after ammonium sulfate precipitation; determination of the chol-DH activity as described in example 3a)) was obtained.

b) Isolation from the biomasses 50 mM potassium phosphate buffer pH 7.0 was used as the standard buffer for all cell disruptions (lysis buffer).

Gaulin press:

4 g deep-frozen biomass (wet weight) was thawed in 40 ml lysis buffer containing 1 mg/ml lysozyme and incubated for 30 minutes. The disruption was achieved at 1000 bar. The DNA released during disruption was digested by adding 0.5 mg/ml DNase and 2.5 mg/ml $MgSO_4.7H_2O$ and incubating for 30 minutes at 25° C. The chol-DH can be purified from the supernatant after centrifugation (SS 34, 19,000 rpm, 30 min. 4° C.) as described under a).

Cell mill (IMA disintegrator S)

1 g deep-frozen biomass (wet weight) was thawed in lysis buffer containing 1 mg/ml lysozyme and incubated for 30 minutes at 25° C. Before treatment in the cell mill 10 ml glass beads (⌀0.25–0.30 mm) was added to the mixture. It was disrupted for 2×4 min at 4000 rpm at 4° C. After removing the glass beads the suspension of broken cells was decanted. The glass beads were washed twice with lysis buffer in order to obtain as quantitative a yield as possible. The cell debris were sedimented by centrifugation (SS 34, 19,000 rpm, 30 min, 4° C.). The chol-DH can be purified from the supernatant as described under a).

Membrane extraction

The sediments of the cells from the cell mill or Gaulin press disruption or whole cells (1 g wet weight, deep-frozen) were washed in 5 ml organic solvent (butyl acetate, n-butanol or ethyl acetate) and subsequently with 10 ml lysis buffer. Chol-DH was then extracted from the cell envelope by incubating the washed cells in 5 ml lysis buffer containing 1% Thesit for 30 minutes at 37° C. while stirring in a water-bath. The extraction preparations were centrifuged (SS 34, 19,000 rpm, 30 min, 4° C.) and the chol-DH could be purified from the supernatant as described under a).

EXAMPLE 3

Determination of the chol-DH activity

The enzyme sample was purified as described in example 2a) and subsequently its property of converting cholesterol was evaluated with the following methods.

a) HPLC method

An enzyme test was used to determine the chol-DH activity by quantifying the cholestenone formed in which the enzyme reaction proceeded for a defined time period before it was stopped by adding a protein-denaturing agent. Afterwards the amount of product was determined and expressed as μmol per minute and volume unit of the enzyme solution (=volume activity) or weight unit of the protein (=specific activity).

The cholestenone formed was quantified by HPLC analysis after stopping the chol-DH reaction:

Column: VYDAC 5 C 18-column (warmed to 37° C.)
Mobile solvent: 100% methanol (isocratic)
Flow rate: 1 ml/min
Detection: 210 nm→cholesterol and cholestenone 240 nm→cholestenone
Duration of run: 10 min The following reagents were used:
1. 50 mM methyl-1,4-benzoquinone (in $H_2O$)

2. 0.4% cholesterol solution: 10% 1-propanole, 10% Thesit in 50 mM potassium phosphate buffer pH 7.0
3. $H_2O_{redist}$.
4. glacial acetic acid
5. ethyl acetate

| Pipette into Eppendorf tubes | Blank | Sample |
|---|---|---|
| Enzyme sample (36–40 mU/ml[1]) | 100 µl | 100 µl |
| MBQ (1) | — | 20 µl |
| $H_2O$ (3) | 20 µl | — |
| cholesterol (2) | 100 µl | 100 µl |
| mix and incubate in a water bath at 37° C. (10–60 min), stop subsequently with | | |
| Glacial acetic acid (4) | 15 µl | 15 µl |
| mix and add | | |
| Ethyl acetate | 200 µl | 200 µl |
| extract by shaking for, 30 min on an Eppendorf shaker; centrifuge briefly (Eppendorf centrifuge) and remove upper ethyl acetate phase for HPLC analysis. | | |

[1]chol-DH activity according to example 3 a)

The chol-DH activity is determined as follows:
Firstly a calibration line for the HPLC method was established using cholestenone (dissolved in ethyl acetate).
One unit is the enzyme activity which oxidizes 1 µmol cholesterol per minute to cholestenone under the test conditions (37° C., pH 7.0). In this case the chol-DH activity is derived from the difference between the cholestenone concentrations of the test mixture and the blank (see above).

Volume activity =

$$\frac{\Delta c(\text{cholesterone})[\mu\text{mol/ml}] \cdot 2}{\text{incubation period}[\min]} \cdot \text{dilution factor of the sample}[U/\text{ml}]$$

b) Photometric method
A chol-DH activity test was set up using 2,6-dichlorophenol-indophenol (DCIP) as a redox mediator:

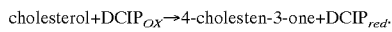

cholesterol+DCIP$_{OX}$→4-cholesten-3-one+DCIP$_{red}$.

It was possible to measure the reduction of DCIP via a decrease in absorbance at 600 nm.

Reagents used:
1. 50 mM $KH_2PO_4$/KOH buffer pH 7.0
2. 0.4% cholesterol solution: 10% 1-propanol, 10% Thesit in 50 mM KPP pH 7.0
3. 4 mM DCIP in buffer (1)
4. catalase (BM cat. No. 0156 744)
5. 10% 1-propanol/Thesit solution in buffer (1)

| pipette into semimicro-cuvettes | Blank | Sample |
|---|---|---|
| buffer (1) | 720 µl | 720 µl |
| DCIP (3) | 25 µl | 25 µl |
| catalase | 5 µl | 5 µl |
| enzyme sample (ca. 10 mU/ml[2]) | 100 µl | 100 µl |
| mix and wait until pre-reaction is completed | | |
| solution (5) | 150 µl | — |
| cholesterol (2) | — | 150 µl |
| mix and measure $A_{600}$ | | |

[2]chol-DH activity according to example 3a)

The chol-DH activity is determined as follows:
One unit is the enzyme activity that oxidizes 1 µmol cholesterol per minute to cholestenone under the test conditions (37° C., pH 7.0) and concomitantly reduces 1 µmol $DCIP_{OX}$.

volume activity =

$$\frac{1.0}{16.13 \cdot 0.1} \text{ dilution buffer of the sample } \Delta A/\min[U/\text{ml sample}]$$

c) Electrochemical method
The chol-DH activity is determined by the quantitative determination of reduced redox mediator on an electrochemical measuring station. Methyl-1,4-benzoquinone is used as the redox mediator.

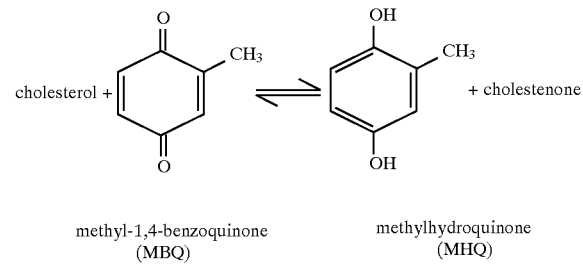

methyl-1,4-benzoquinone (MBQ)     methylhydroquinone (MHQ)

Measurement of the methylhydroquinone formed is carried out on a dummy (plastic support printed with graphite paste) at a measuring voltage of 240 mV.
The following reagents were used:
1. 50 mM methyl-1,4-benzoguinone (in $H_2O$)
2. 0.4% cholesterol solution: 10% 1-propanol, 10% Thesit in 50 mM potassium phosphate buffer pH 7.0
3. $H_2O_{redist}$.
4. glacial acetic acid

| Pipette into Eppendorf tubes | Blank | Sample |
|---|---|---|
| Enzyme sample (0.1–0.2 U/ml[3]) | 50 µl | 50 µl |
| MBQ (1) | — | 10 µl |
| $H_2O$ (3) | 10 µl | — |
| cholesterol (2) | 50 µl | 50 µl |
| mix and incubate in a water bath at 37° C. (10–30 min), stop subsequently with | | |
| Glacial acetic acid (4) | 7 µl | 7 µl |
| Measure the current until constant (ca. 2.5 min) on dummy | | |

[3]chol-DH activity according to example 3 a)

The chol-DH activity is determined as follows:
Firstly a calibration line was established under the test conditions using methylhydroquinone as a standard. Δc (MHQ) is calculated from the difference between the MHQ concentration of the blank and the sample.
One unit is the enzyme activity that oxidizes 1 µmol cholesterol per minute to cholestenone under the test conditions (37° C., pH 7.0) and concomitantly reduces 1 µmol methyl-1,4-benzoquinone to methylhydroquinone.

$$\text{volume activity} = \frac{2.34}{t} \cdot F \cdot \Delta c(MHQ)[U/\text{ml}]$$

$F$ = dilution factor of the sample d) Variation of the redox mediators used
Apart from methyl-1,4-benzoquinone other redox mediators are suitable as electron acceptors for chol-DH. The chol-DH activity was determined by the HPLC method. Various redox mediators are listed in Table 1 that can serve as artificial electron acceptors for chol-DH.

TABLE 1

| Mediator | chol-DH [%] |
| --- | --- |
| methyl-1,4-benzoquinone (MBQ) | 100 |
| p-benzoquinone (PBQ) | 109 |
| tetrachloro-p-benzoquinone | 27 |
| 2,6-dichlorophenol-indophenol (DCIP) | 52 |
| N,N-dimethyl-1-4-nitrosoaniline (NA) | 95 |
| N,N-bis-2(hydroxyethyl)p-nitrosoaniline | 45 |

EXAMPLE 4

Determination of the Cholesterol Concentration

With the aid of the following test sequence it was shown that the chol-DH according to the invention is suitable for determining the cholesterol concentration:

Reaction scheme:

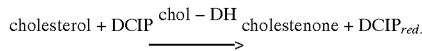

cholesterol + DCIP $\xrightarrow{chol-DH}$ cholestenone + DCIP$_{red}$.

Reagents used:
1. 50 mM KH$_2$PO$_4$/KOH buffer pH 7.0, 1.5% 1-propanol, 1.5% Thesit
2. 4 mM DCIP in buffer (1)
3. catalase (BM cat. No. 0156 744)
4. chol-DH solution: 1 U/ml (final concentration; determined according to example 3a) in 50 mM KH$_2$PO$_4$/KOH buffer pH 7.0

Procedure:
The decrease in absorbance is measured at 600 nm
Measuring radiation: 600 nm Path length: 1.0 cm
Test volume: 1.0 ml Measuring temperature: 37° C.

| Pipette into semimicro-cuvettes: | |
| --- | --- |
| buffer (1) | 770 μl |
| DCIP (2) | 25 μl |
| catalase (3) | 5 μl |
| chol-DH solution (4) | 100 μl |
| mix, incubate, add | |
| cholesterol sample | 100 μl |
| mix and measure A$_{600}$ after 30 minutes | |

Calculation:

$$\Delta A \cdot \frac{1.0}{16.13 \cdot 0.1} = \mu mol/ml \text{ sample solution}$$

EXAMPLE 5

Chol-DH activity at various oxygen saturations

The chol-DH activity was measured by means of the HPLC method (example 3a)) under reduced oxygen, atmospheric and oxygen-saturated conditions. A reduction in oxygen was achieved by degassing the test mixtures (10 min) and subsequently gassing with nitrogen (10 min). Furthermore, the test procedure is carried out in an anaerobic chamber. Saturation with oxygen was achieved with the aid of an O$_2$-regenerating system by adding H$_2$O$_2$ (0.01% final concentration in the test system) and catalase (40 U/ml final concentration in the test system).

It turned out that oxygen does not interfere with the test (Tab.2).

TABLE 2

| O$_2$ conditions | Chol-DH [U/ml] |
| --- | --- |
| reduced | 13.3 |
| atmospheric | 13.7 |
| saturated | 13.7 |

We claim:

1. An isolated, cholesterol converting enzyme having cholesterol dehydrogenase activity, wherein said cholesterol converting enzyme oxidizes cholesterol by removing electrons from cholesterol and transferring said electrons to an artificial electron acceptor, wherein the transfer of said electrons does not require oxygen, said cholesterol converting enzyme having a molecular weight of approximately 55000 Da as determined by SDS-PAGE, wherein said cholesterol converting enzyme is an Actinomycetes or a Basidiomycetes cholesterol converting enzyme.

2. The insulated, cholesterol converting enzyme according to claim 1, wherein said artificial electron acceptor is selected from the group consisting of benzoquinone, indophenol and nitrosoaniline.

3. The isolated, cholesterol converting enzyme according to claim 2 wherein said electron acceptor is selected from the group consisting of methyl-1,4-benzoquinone, p-benzoquinone, N,N-dimethy-4-nitrosoaniline, 2,6-dichlorophenol-indophenol and N,N-bis-2(hydroxyethyl)p-nitroso-aniline.

4. The isolated, cholesterol converting enzyme according to claim 1, wherein said enzyme has a residual activity of at least 90% after about 30 minutes at 60° C. in a pH range of from about 7.0 to about 8.0.

5. The isolated, cholesterol converting enzyme according to claim 1, wherein said enzyme has an isoelectric point of about 8.6.

6. The isolated, cholesterol converting enzyme of claim 1, having highest stability at a pH of 7.0 to 8.0.

7. An isolated, cholesterol converting enzyme having cholesterol dehydrogenase activity, wherein said enzyme oxidizes cholesterol by removing electrons from cholesterol and transferring said electrons to an artificial electron acceptor, wherein the transfer of said electrons does not require oxygen, said isolated cholesterol converting enzyme being obtained from a microorganism selected from the group consisting of Rhodococcus BMTU 3899, DSM 9444, *Rhodococcus erythropolis*, DSM 743; *Streptomyces hydgroscopicus*, DSM 40771, *Flammulina velutipes*, DSM 1658; *Coprinus comatus*, DSM 1746; and *Trametes versicolor* BMTU 3107, DSM 9443.

\* \* \* \* \*

UNITED STATES PATENT AND TRADEMARK OFFICE
CERTIFICATE OF CORRECTION

PATENT NO. : 5,856,156
DATED : Jan. 5, 1998
INVENTOR(S) : Ambrosius et al.

It is certified that error appears in the above-identified patent and that said Letters Patent is hereby corrected as shown below:

In column 2, line 49, change "Samlung" to -- Sammlung --.
In column 9, line 17, change "for, 30 min." to -- for 30 min. --.
In column 9, line 32, change "Δc (cholesterone)" to -- Δc (cholestenone) --.
In column 10, line 30, change "benzoguinone" to -- benzoquinone --.
In column 12, line 55, change "hydgroscopicus" to -- hygroscopicus --.
In cover page, in the section entitled U.S. Patent Documents, line 1, change "5,128,247" to -- 5,126,247 --.

Signed and Sealed this

Twenty-second Day of May, 2001

Attest:

NICHOLAS P. GODICI

Attesting Officer     Acting Director of the United States Patent and Trademark Office